United States Patent [19]

Nolan et al.

[11] 4,195,665

[45] Apr. 1, 1980

[54] FLUID VALVE

[75] Inventors: Gaillard R. Nolan, Acton; William E. Flynn, Chelmsford, both of Mass.

[73] Assignee: Instrumentation Laboratory, Inc., Lexington, Mass.

[21] Appl. No.: 881,000

[22] Filed: Feb. 24, 1978

[51] Int. Cl.² .............................................. C01N 1/10
[52] U.S. Cl. ........................ 137/624.18; 137/625.11; 137/627; 137/876; 73/423 A
[58] Field of Search ............ 137/625.11, 624.18, 137/624.2, 876, 627; 73/424, 423 A, 421 R; 251/160, 161

[56] References Cited

U.S. PATENT DOCUMENTS 3,536,098  10/1970  Cunningham .................. 137/876

FOREIGN PATENT DOCUMENTS

1922429  11/1970  Fed. Rep. of Germany ...... 137/625.11
2436595  12/1976  Fed. Rep. of Germany ...... 137/625.11
 939965  10/1963  United Kingdom ............. 137/625.11

*Primary Examiner*—Alan Cohan

[57] ABSTRACT

The fluid valve essentially comprises a support structure designed rotatably to support an inlet within a certain oscillatory ambit and stationarily supporting a plurality of outlets within the oscillatory ambit, and operative means for effecting fluid-tight communication seriatim between the inlet and one of the outlets. The inlet is preferably a blunt needle provided with a side port and each of the outlets comprises an inverted "Y"-shaped member formed of an entrance portion and a pair of leg portions. The needle is designed to be thrust into the entrance portion, so that its side port establishes fluid-tight communication with one of the leg portions. Means are provided, including a pneumatic cylinder, for effecting relative motion between the inlet and the outlets. There is also a means for normally closing off all the entrance portions of the outlets except the selected one, and only during the entry of the blunt needle therein. Such means includes a plurality of pinch rods and a cylindrical cam mounted about the pneumatic cylinder and provided with a channel to cooperate with one end of the pinch rods so as to open the selected outlet when the needle is thrust therein. Means are also provided for selectively indexing the needle within the oscillatory ambit which comprises both electrical and mechanical parts.

33 Claims, 12 Drawing Figures

FLUID VALVE

BACKGROUND OF THE INVENTION

In the use of automatic analysis apparatus designed to make diverse measurements of fluid samples such as biological fluids, atmospheric air, gases or the like, it becomes necessary to introduce a fluid sample emanating from a single source and to direct discrete amounts of that sample to one or more or all of a plurality of independent and separate measuring systems wherein each system is designed to measure the sample for a particular constituent thereof. For example, one system may be designed to measure for the partial pressure of carbon dioxide, another for total hemoglobin, another system for BUN, a further system for creatinine, another for percentage of carboxyhemoglobin, another for total chloride, etc. Each of such systems requires that a discrete small amount of the sample be carried to it in relatively rapid succession, so that the cycle time of the automatic analysis apparatus remains within manageable and acceptable limits.

Some heretofore known fluid valves were of the face valve type and presented serious sealing problems. Concurrent with such sealing problems were seepage and consequent contamination and carryover between successive samples. More often than not, such fluid valves had to be dismantled in order to be cleaned. Furthermore, heretofore known valves did not allow for the independent operation of each of the separate and independent fluid systems connected thereto. All this contributed to an excessive cycle time, and also presented extensive down times for the automated apparatus during the time periods required to disassemble and thoroughly clean the fluid valve.

The fluid valve of the invention is designed to obviate the above shortcomings by providing a relatively simple valve designed to channel small and discrete amounts of fluid samples from one outlet to a plurality of outlets in such a manner that it can be easily, thoroughly and swiftly cleaned inbetween delivery of different samples, so that there is no significant carryover from one sample to the next. Furthermore, the design of the valve permits operation of each of the plurality of separate fluid systems connected to the valve independent of all other fluid systems as well as any unrelated valve action. The valve of the invention also eliminates sealing problems heretofore associated with fluid face valves.

PRIOR ART STATEMENT

A search of the known prior art revealed no similar fluid valve used in the fluid supply system of analysis apparatus and designed automatically to switch fluid samples in discrete amounts from a single inlet to a plurality of outlets in which each of these outlets communicates with and also forms a part of an entirely separate and independent fluid system.

What the prior art did reveal is apparatus which do pick up a sample in a precise given amount and deliver that sample to an automatic analysis instrument, with or without mixing along the way. Thus there is a single inlet in the prior art which communicates essentially with a single outlet representing a single fluid system, but not a multiplicity of fluid systems.

U.S. Pat. No. 3,858,450 granted Jan. 7, 1975, to A.R. Jones, entitled "Sample Mixing and Metering Apparatus," discloses a sampling head including a hollow pickup probe for extracting a given amount of sample from a cup. The probe is movable between a sampling position and a retracted position. A valve mechanism connected to the probe is basically of the face-valve type in which two blocks are designed linearly slidable relative to each other between two valve positions, namely a sampling position and a delivery position. The air cylinder moves not only the probe but also operates this sliding valve. In the delivery position, the valve effects fluid connections for mixing a given amount of the sample with another fluid and for simultaneously delivering the mixture to a receptacle.

U.S. Pat. No. 3,900,289 that issued to M. D. Liston on Aug. 19, 1975, entitled "Apparatus and Method for Filling a Compartment," discloses essentially a specimen dispenser designed to fill a compartment to a predetermined level with an aqueous solution taken from a reservoir. The dispenser includes a hollow probe nozzle designed to withdraw solution from the reservoir which is then moved to the vicinity of the compartment in order to deposit a predetermined amount of the solution into the compartment.

U.S. Pat. No. 3,940,995 that issued to R. J. Harris, Sr. et al. on Mar. 2, 1976, and entitled "Automatic Fluid Injector," discloses an injector designed for accurately measuring and injecting quantities of fluid specimens into various media, e.g., a receptacle or an inlet of a modern analytical instrument. The injector includes the combination of essentially three subassemblies, namely (a) a syringe assembly including a needle, (b) an injector feed assembly for automatically and continuously purging, cleaning and filling the syringe, and (c) a feed tray for transporting specimen-containing vials to the injector feed assembly for pickup for the specimen and delivery to the syringe of the injector. It discloses means for moving that syringe along a straight path for insertion and withdrawal thereof from the inlet of an analytical instrument and a reciprocable hollow probe designed to pick up fluid specimen from a vial, and to convey the specimen to the syringe. A valved line is provided at the forward end of the barrel surrounding the syringe needle through which an initial portion of the specimen is passed to remove contaminants from previous specimens. By means providing for the withdrawal of the plunger of the syringe to a predetermined position, the syringe is enabled to withdraw an accurately-measured portion of the specimen. Just prior to injection, the previously-mentioned valved line is closed, the syringe is carried forward to insert the needle through the inlet of an analytical instrument, followed by sample injection, and then the needle is withdrawn. Automatic controls are provided for cyclically cleaning, purging, filling and injecting fluid specimens into the analytical instrument.

As noted, the known prior art is devoid of a fluid valve which is provided with a single inlet that can communicate with a plurality of outlets in which each of these outlets communicates with and also forms part of a separate and independent fluid system, meaning that each such fluid system in essence represents a separate and independent analytical instrument designed to subject the specimen to an independent analysis for an entirely different constituent of interest of the specimen.

SUMMARY OF THE INVENTION

In summary, the invention pertains to a multiposition fluid valve which may be used in the fluid supply system of an automatic analysis apparatus, which apparatus is designed to measure a specimen sample such as a biological fluid, namely blood, urine or spinal fluid, for a multiplicity of its constituents of interest, or to such a fluid valve having industrial applications or applications in which the valve is used to distribute a solution or slurry being measured for its constituents. These constituents of interest may be any one or more or all of two or more dozen of such items, depending upon the particular automatic analysis apparatus of which the fluid valve of the invention forms a part. Some of such constituents of interest may include, by way of example and not limitation: creatinine, glucose, uric acid, triglyceride, BUN, chloride, magnesium, total bilirubin, total protein, albumin, calcium, phosphate, potassium, sodium, lithium, amylase, etc., all as well known in the art.

The basic function of the fluid valve of the invention resides in taking a fluid sample from a single source such as a vial containing a patient's sample specimen and then switching discrete and exact amounts thereof to one or more or all of a plurality of separate and independent fluid subsystems in which each such independent fluid subsystem is designed to measure for a specific one of the above-indicated constituents.

It becomes of course of paramount importance that cross-contamination between fluid samples of different patients admitted to the automatic instrument one after the other is prevented. Such carryovers are normally associated with systems heretofore employed wherein great care must be exercised in purging the previous sample from the system, followed by a thorough cleaning before admitting the next succeeding sample, or some sort of compensation must be built into the system combined with use of bubbles for partial cleaning, making for a relatively expensive and cumbersome procedure at best.

The fluid valve of the invention essentially comprises a support structure which is designed to support a single inlet means for oscillatory motion within a set oscillatory ambit, and also to support a plurality of outlet means that are stationarily mounted thereon and within the oscillatory ambit of the inlet means. It is to be understood that each one of these outlet means also forms a part of and communicates with a separate and independent fluid subsystem of the automatic analysis apparatus, as above described.

The fluid valve of the invention is provided further with a means for normally closing off each of these outlet means and, also with means for effecting relative motion between the single inlet means and a selected one of the outlet means. Such means for effecting relative motion includes a pneumatic cylinder whose longitudinal axis represents also the axis of the oscillatory motion of the inlet means. The means for normally closing off the outlet means further includes a cylindrical cam concentrically mounted about the pneumatic cylinder and having a channel provided in the outer surface thereof and in parallel with its longitudinal axis and, a plurality of pinch rods operatively mounted adjacent the outlet means in a plane normal to the longitudinal axis and radially projecting therefrom in such a manner that one end of each of these pinch rods is designed to be accommodated within that channel.

There is also a means provided for selectively indexing the inlet means within the above-mentioned oscillatory ambit thereof so as to line it up with one of the outlet means. This means may, for instance, essentially comprise a motor for imparting the oscillatory motion to the inlet means, a means for arresting the oscillatory motion in line with one of these outlet means, a guide member mounted adjacent the inlet means and being oscillatory therewith, and a plurality of guide slots designed selectively to accommodate therein the guide member, whereby the inlet means is precisely aligned with one of the outlet means when the relative motion is effected therebetween.

Basically, the inlet means consists of a hollow blunt needle provided with a suitable side exit port and each of the plurality of outlet means comprises an inverted "Y"-shaped member having an entrance portion and a pair of leg portions so that when the needle is fully thrust therein, its side exit port effects fluid-tight communication with one of the leg portions. Although for most applications it is not required, the fluid valve of the invention is also provided with a means for also closing off one of these pairs of leg portions of the "Y"-shaped members. Essentially such a means comprises a plunger mounted adjacent the guide member which is designed to cooperate with an actuator member and, a pair of pins to effect pinching off one leg of the pair of leg portions when the plunger bears against and displaces the actuator member, as will be more fully explained below.

Thus, the invention pertains to a multi-position fluid valve that is relatively simple in construction, is easily and effectively cleaned inbetween samples and, that accomplishes its intended function of delivering from a single source discrete amounts of a fluid sample to one or more or all of a series of independent fluid subsystems represented by individual outlet means.

BRIEF DESCRIPTION OF THE DRAWINGS

These and other advantages and features of the present invention will hereinafter appear for purposes of illustration but not by way of limitation in connection with the accompanying drawings, in which like reference numerals refer to like parts throughout and in which.

DETAILED DESCRIPTION OF PREFERRED EMBODIMENT

Figure 1:
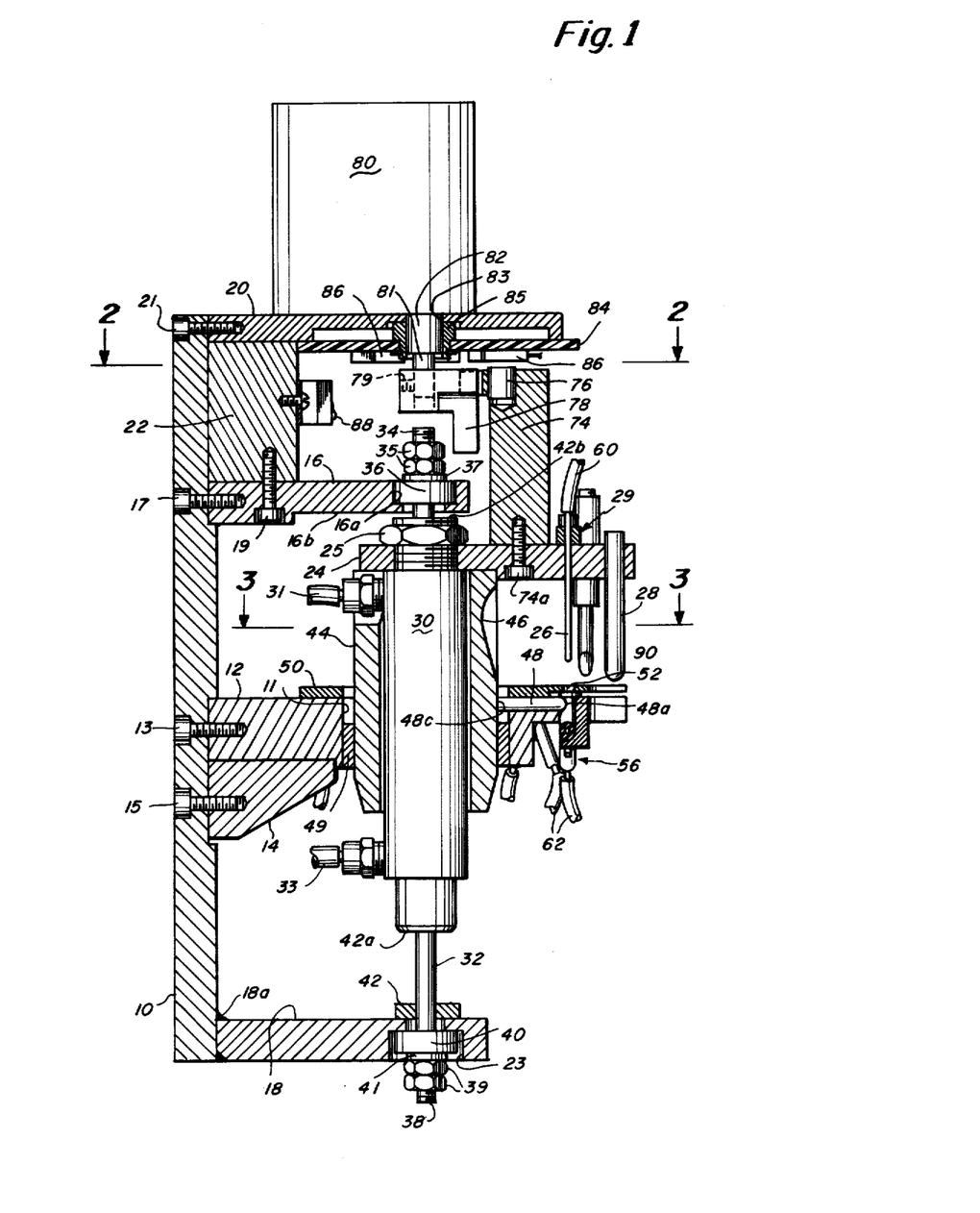
FIG. 1 is a side elevational view, partly in section, of the multi-position fluid valve of the invention and representing a preferred embodiment thereof.

Referring now to the drawings in greater detail, the preferred embodiment of the multi-position fluid valve of the invention is shown in side elevation and partly in section in FIG. 1. The fluid valve is designed to be securely mounted to the frame of an automatic analysis apparatus designed to analyze fluid samples for a plurality of constituents of interest.

The fluid valve is essentially built about and is supported by a main support structure 12 that may be conveniently affixed to a frame 10 by means of a screw 13. In order more securely to mount the structure 12 to the frame 10, a further support 14 is also mounted just below the main support structure and is secured to the frame by a further screw 15. As may be observed, the main support structure 12 basically holds the operative elements of the fluid valve of the invention in cantilever style and within an upper support arm 16 secured to the frame 10 by screw 17 and a lower support arm 18 secured to the frame 10 in any convenient manner, as by being welded thereto as shown at 18a.

The main support structure 12 is provided with a circular opening 11 rotatably accommodating therein, and also for vertical motion, a double-acting pneumatic cylinder 30 having suitable connections to a source of pneumatic pressure (not shown) by means of connectors 31 and 33. The piston rod 32 of the cylinder 30 is shown securely anchored in lower ball bearings 40 accommodated within a suitable opening 23 formed in the lower support arm 18 and secured therein by means of a suitable washer 41 and two internally threaded nuts 39 cooperating with the externally threaded lower end 38 of the piston rod 32. A loose fitting stroke-limiting ring 42 is positioned about piston 32 and resting on the lower support arm 18, which ring 42 by its thickness is designed to limit the downward travel of the cylinder 30 which is reached when surface 42a strikes the ring 42. The upper externally threaded end 34 of the cylinder's shaft is anchored in upper ball bearings 36 located within a suitable opening 16a formed in the upper support arm 16, and secured therein by means of a suitable washer 37 and a pair of internally threaded nuts meshing with the externally threaded portion of the cylinder shaft 34. The extent of the upper travel of cylinder 30 is governed by the length of piston rod 32 and care must be taken that surface 42b does not strike against the underside 16b of the upper support arm 16, but rather that there is some clearance therebetween.

A rotating arm 24 is secured to the upper end of the double acting cylinder 30 by means of a lock nut 25, with arm 24 also securing a cylindrical cam 44 about the outer periphery of the cylinder 30 and accommodated therewith within the opening 11 of the main support structure 12 by means of a suitable bushing 49. It is to be understood that rotating arm 24, cylinder 30 and cylindrical cam 44 act together in unison, namely that when one is rotating and/or is moving vertically up and down, they all do the same and at the same time. The significance thereof will be more further evident as the description continues. It should be also noted that cylindrical cam 44 is provided with a channel 46 which is formed in its surface in parallel with its longitudinal axis and is of generally square-shaped cross section, as may be best noted in FIG. 3. Furthermore, channel 46 is designed with a curve angle so that its depth varies along its length substantially as shown in FIGS. 1 and 4, the significance of which will become more apparent below.

Figures 4, 5:
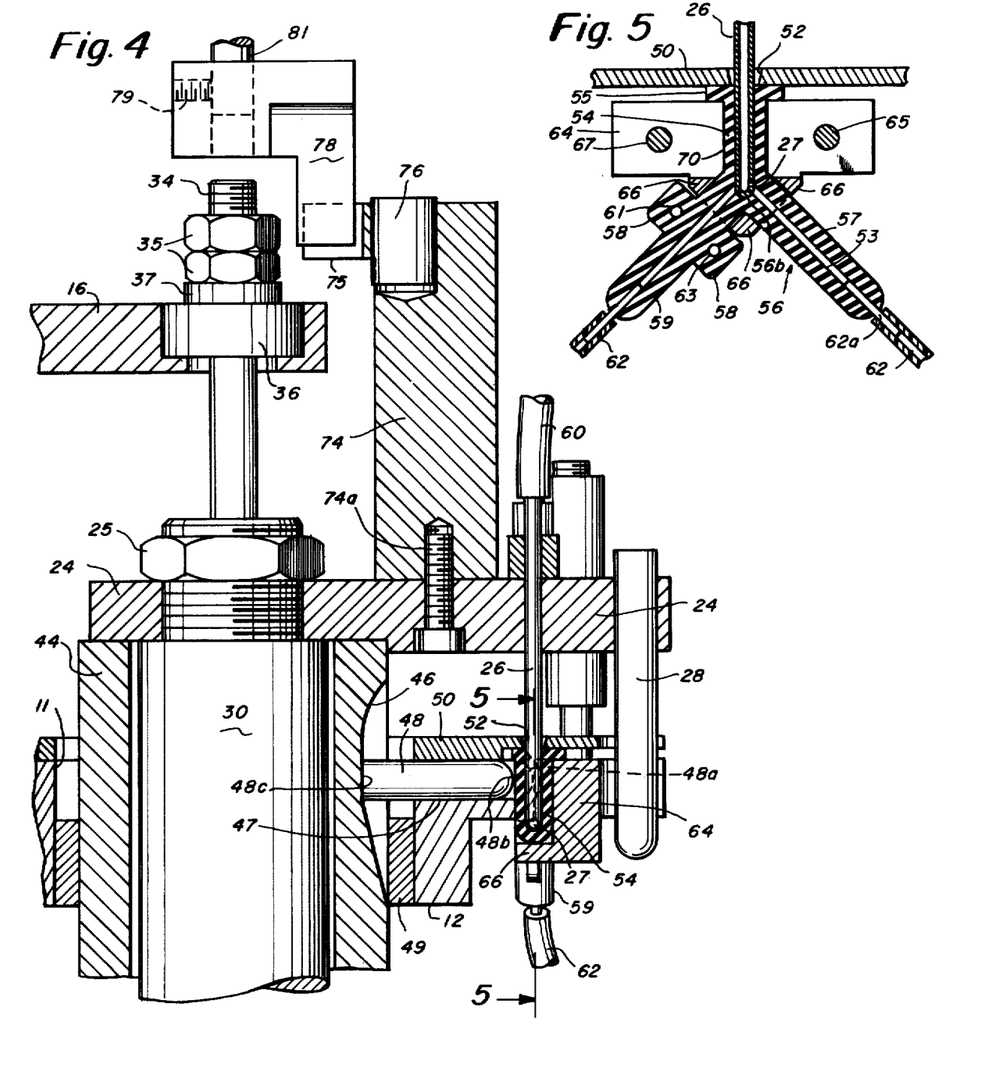
FIG. 4 is a fragmentary side elevational view, partly in section and on an enlarged scale, and specifically showing the position of the single inlet means represented by a blunt needle when the same is thrust into one of the outlet means represented by an inverted "Y"-shaped member and showing also the entrance portion of the outlet means being open by having its associated pinch rod accommodated within a channel provided in the outer surface of a cylindrical cam.
FIG. 5 is a vertical section, partly in elevation, and taken along the line 5—5 of FIG. 4 and in the direction of the arrows, depicting one of the outlet means represented by an inverted "Y"-shaped member, with the inlet means represented by a blunt needle thrust into its entrance portion.

The rotating arm 24 carries with it, among others, the single inlet means 26 which is essentially a hollow blunt needle provided with a side exit port 27, as may be best observed in FIGS. 4 and 5. This single inlet means 26 is secured in the rotating arm 24 by means of a needle clamp assembly 29 provided with a screw 29a, as may be best observed in FIG. 2. A flexible inlet tube 60 is connected to the upper free end of the inlet means 26 by means of which it is connected to a suitable single source which may be represented by a probe such as for instance disclosed in U.S. Pat. No. 3,858,450 granted to Jones on Jan. 7, 1975 and reference therein by the numeral 22. By immersing such a probe into a vial containing a fluid specimen in a manner well known and which does not form a part of the present invention, a fluid sample is introduced through such probe and by means of the flexible inlet tube 60 to the single inlet means 26.

The main support structure 12 is furthermore designed to accommodate a number of suitably shaped clamp blocks 64, with each of these clamp blocks 64 being removably secured to the main support structure 12 by means of a pair of bolts 65 and 67. The configuration of one such clamp block 64 may be best described with reference to FIGS. 3, 4 and 5. The basic function of each of these clamp blocks 64 is removably and securely to accommodate therein an outlet means 56 which is essentially formed like an inverted "Y"-shaped member from a suitable elastomeric material such as neoprene or synthetic rubber.

Each of these outlet means 56 is shaped with an entrance portion 54 having a suitable flange 55 serving to keep in cooperation with plate 50 the outlet means 56 in place when the inlet means 26 is withdrawn therefrom and by means of which it may rest against the upper surface of the clamp block 64 when the inlet means 26 is inserted therein, with the entrance portion 54 being accommodated within a semi-circular channel 70 of the clamp block 64. The entrance portion 54 in turn is connected to a pair of leg portions 57 and 59 and, of course, both the entrance and leg portions are provided with a communicating internal channel 53 formed concentrically in member 56.

In order to securely hold the lower end of the entrance portion 54 and each of the leg portions 57 and 59 in their desired inverted "Y"-shaped, three suitably formed horizontally supporting projections 66 are provided as an integral part of the clamp block 64 and protrude therefrom, substantially as shown in FIGS. 4 and 5, to provide the necessary bottom and side supports for the outlet means 56. As may be observed, when the single inlet means 26, i.e., the blunt needle, is fully inserted into the entrance portion 54 of the outlet means 56, its side exit port 27 is in fluid-tight communication with the internal channel 53 of one of the leg portions 57 and the end of the blunt needle deforms slightly, as at 56b, the apex of the internal channel 53. Suitable flexible tubings 62 are connected to each of the leg portions 57 and 59 by appropriate metal tubular connectors 62a. These tubes 62 are in turn connected to separate and independent fluid subsystems of the overall automatic analysis apparatus of which the multi-position fluid valve of the present invention forms but a part. One of the leg portions 59 of the outlet means 56 may also be provided with an integral pair of side flaps 58, provided with respective holes 61 and 63 therein, the function of which will be best described with reference to FIGS. 6, 7 and 12.

It is essential for the operation of the fluid valve of the invention that each of these outlet means 56 is normally closed off at its entrance portion 54, except when the inlet means 26 is thrust into it as shown in FIGS. 4 and 5. Such means for normally closing off such outlet means 56 comprises, in combination, the cylindrical cam 44 already mentioned and described together with its channel 46 and a plurality of pinch rods 48 operatively mounted adjacent each of the outlet means 56 within suitable openings 47 radially formed in the main supporting structure 12, as may be best observed in FIGS. 3 and 4. Access to these pinch rods 48 may easily be gained by the removal of plate 50 secured to the top of the main support structure 12 by a number of screws 51, as may be best observed in FIG. 3. One end 48c of each of these pinch rods is designed to be accommodated within the channel 46 of cam 44 and the other end, 48b, which is preferably rounded, is normally pressing against the entrance portion 54 of the outlet means 56 as shown with broken lines in FIG. 4 as at 48a. The fully-opened position for the outlet means 56 is depicted in solid lines in FIG. 4 when end 48c is at its deepest penetration within channel 46.

It is to be noted especially with reference to FIG. 1 that when the inlet means 26 is not in contact with the outlet means 56, i.e., when the double acting pneumatic cylinder 30 is in its uppermost position as shown, the inner ends 48c of each of the pinch rods 48 contact and ride on the outer periphery of the cylindrical cam 44 and are thus pressed against the entrance portions 54 of each of the outlet means 56 so as to close these off. In such position, leg portions 57 and 59 of each of these outlet means 56 are of course open, i.e., the internal channel 53 therein is in fluid communication from one leg to the other, so that fluid may be transmitted therethrough in either direction within the particular independent and separate fluid subsystem of which each of such outlet means 56 forms also a part.

The upper support arm 16 is further anchored by screw 19 to a bar 22 designed to carry a pair of "stop" micro-switches 88 whose function will become more apparent with a description of the operation of the fluid valve. Bar 22 also supports, together with a suitable screw 21, the top motor support plate 20, supporting a suitable electric motor 80 thereon, whose basic function is to provide the oscillatory motion to the rotating arm 24 and to the thereto connected parts. Motor 80 transmits this motion through its shaft 81 accommodated within suitable bearings 82 mounted within an opening 83 formed in the top plate 20. Suitable bushing 85 locates a printed circuit board 84 for concentricity and angular adjustment. Shaft 81 is in turn secured to an inverted "L"-shaped arm 78 by means of a set screw 79, as may be best observed with reference to FIG. 2 and 4. A post member 74, preferably made of a nonmagnetic material and provided with a pair of shoulders 75, is designed to surround thereby the inverted "L"-shaped arm 78 and to permit relative motion in vertical translation between the shoulders 75 and the "L"-shaped arm 78 therein. Post 74 at its lower end is firmly anchored to the rotating arm 24 by a suitable screw 74a. At its upper end and adjacent the shoulders 75, post 74 also accommodates a magnet 76, whose function will become apparent from a description of the operation of the valve of the invention.

Figure 2:
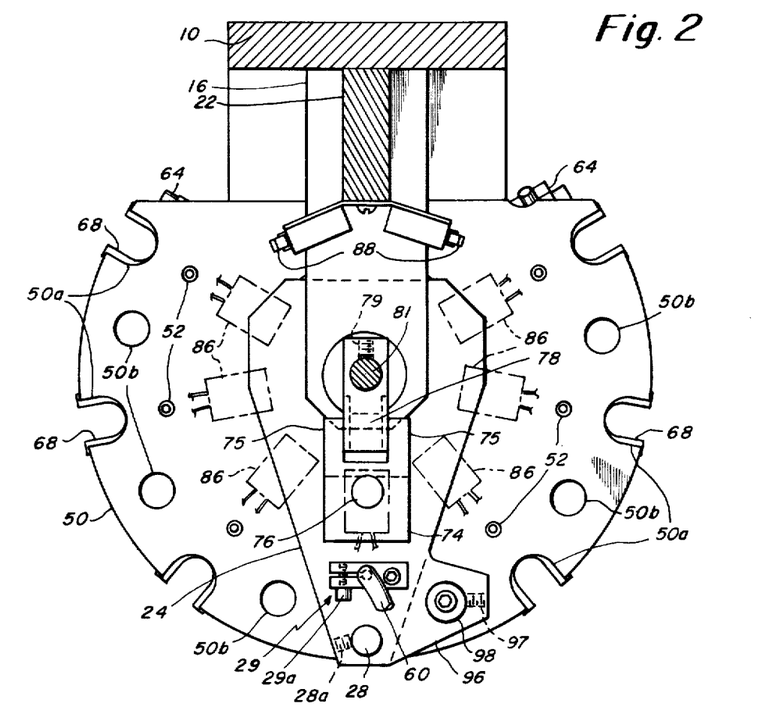
FIG. 2 is a sectional plan view taken along the line 2—2 of FIG. 1.

At the underside of the top motor support plate 20, the printed circuit board 84 surrounding the bearings 82 is designed to carry a plurality of "Hall"-effect switches 86, one each such switch 86 being provided for each outlet means 56 and arranged substantially radially aligned with each of the outlet means 56, as may be best observed with reference to FIG. 2, where the "Hall"-effect switches 86 are shown in broken lines. These "Hall"-effect switches are designed, as is well known, to cooperate with the magnet 76 mounted in post 74 to arrest the oscillatory motion of the rotating arm 24 in such a manner as to sustantially align the single inlet means 26 with a selected one of the outlet means 56. Precise alignment of the inlet means 26 with the hole 52 in the plate 50 and the entrance portion 54 of the underlying inverted "Y"-shaped member 56 representing the outlet means is effected by a suitable guide member 28 secured by a set screw 28a within the rotating arm 24. Guide member 28 is a bit longer than blunt needle 26 and is thus the first part which approaches the plate 50.

Figure 3:
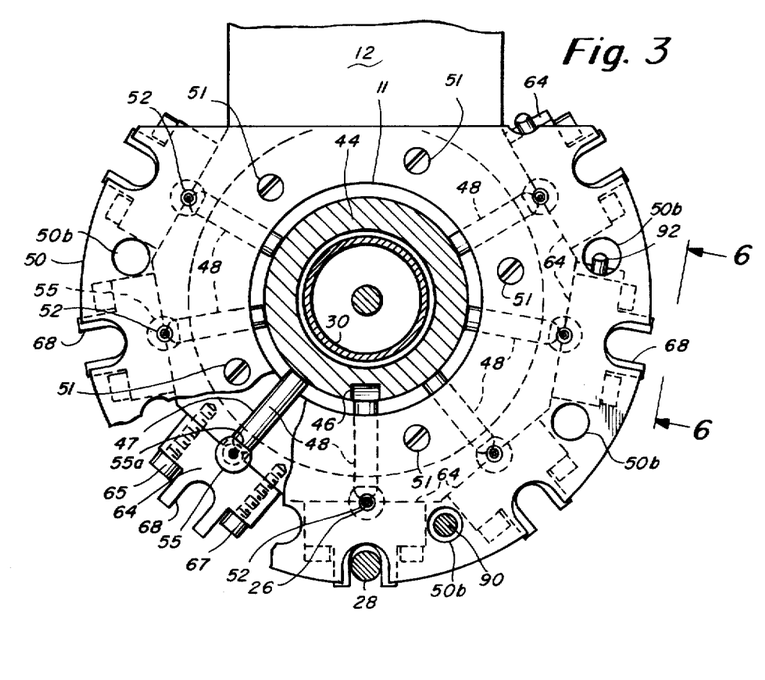
FIG. 3 is a view similar to FIG. 2, but is a fragmentary sectional plan view taken along the line 3—3 of FIG. 1.

Guide member 28 is designed to cooperate with a plurality of guide slots 68 formed in each of the clamp blocks 64, as best shown with reference to FIG. 3. These guide slots are radially precisely aligned with the semicircular channels 70 formed therein which accommodate the inverted "Y"-shaped members 56 defining the outlet means. By entering into and being guided by these guide slots 68, guide member 28 precisely aligns the single inlet means 26 represented by a blunt needle so that it can securely enter, first through hole 52 in plate 50, and then into the underlying entrance portion 54 of the respective "Y"-shaped member 56, as may be best observed with reference to FIGS. 4 and 5.

Plate 50, in addition to being provided with the already mentioned small holes 52 to permit passage therethrough of the single inlet means 26, is also provided with a plurality of "U"-shaped openings 50a which are somewhat larger than the guide slots 68, as may be best noted from a view of FIGS. 2 and 3. Plate 50 is also provided with a plurality of large holes 50b, the significance of which will become apparent in connection with the modification shown in and described with reference to FIG. 6 below. One of the functions of plate 50 is to secure the several pinch rods 48 within their respective openings 47 and also to clamp the flanges 55 of the inverted "Y"-shaped members 56 therebetween and the upper surface of the clamp blocks 64, as may be best observed in FIG. 5. The flanges 55 may, furthermore, be formed with a flat side 55a (observe FIG. 3) so as to facilitate the orientation of the "Y"-shaped member 56 with respect to both the pinch rods 48 and clamp blocks 64 Thus, each of these outlet means 56 is securely held in place and yet may be easily replaced whenever normal wear and tear so requires by simply unscrewing bolts 65 and 67 of the particular clamp block 64 so as to release the "Y"-shaped member from the semi-circular channel 70 formed therein.

Figure 6:
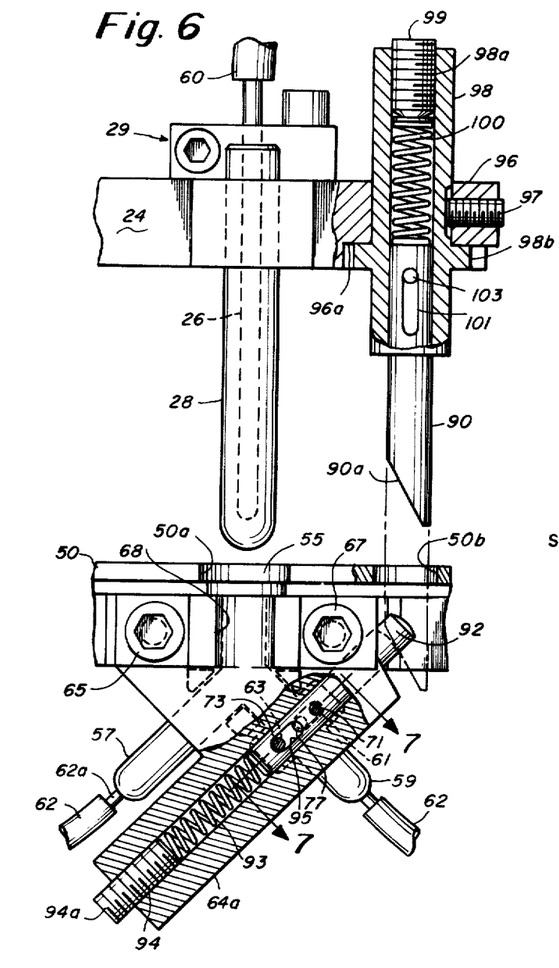
FIG. 6 is a vertical front elevational view partly in section, on a much enlarged scale, and taken along the line 6—6 of FIG. 3 and in the indicated direction and, depicting especially a further means designed for closing off one of the pair of leg portions of the inverted "Y"-shaped members.
Figure 7:
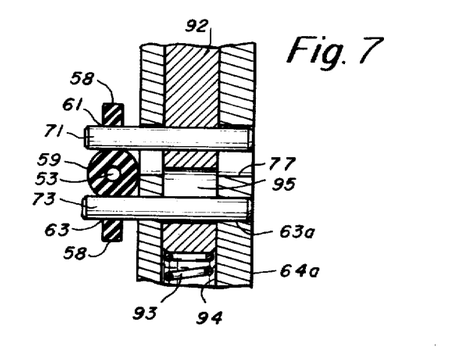
FIG. 7 is a fragmentary sectional view taken along the line 7—7 of FIG. 6 and in the indicated direction.

FIG. 6 depicts essentially the provision of a further means designed in instances where so desired for closing off one leg portion 59 only of the pair of leg portions of the inverted "Y"-shaped members 56, but only at the time when the single inlet means represented by the blunt needle 26 is thrust into the entrance portion 54 of the outlet means, as will now be described more fully and with additional reference to FIGS. 7 and 12.

This further means to close off one of the pair of leg portions basically comprises a plunger 90, designed to enter through hole 50b in plate 50 so as to engage the free end of actuator member 92 by its beveled portion 90a riding thereagainst as shown in phantom lines in FIG. 6. The construction of plunger 90 is such, however, that upon initial contact by its beveled portion 90a with the upper free end of the actuator member 92, plunger 90 depresses actuator member 92 to full depth using pressure from spring 100 and, as the actuator member 92 bottoms, spring 100 compresses and allows arm 24 and its attached parts to continue moving downward to required depth. This is due to the cooperative action of a pin 103 provided in the side of the plunger which is permitted to slide within a slot 101 the whole length thereof. Plunger 90 is maintained in its normally extended position, as shown in FIG. 6 in solid lines, by a compression spring 100 mounted within plunger housing 98 and kept under compression by an externally-threaded plug 99 screwed therein and cooperating with an internally threaded bore 98a of the housing. Plug 99 provides for adjustment of compression.

Plunger 90 and the above-mentioned parts are arranged within a suitable support structure 96 which may be formed as an integral part of the rotating arm 24, as shown in FIG. 2, or which may be secured thereto by suitable means, such as screws not shown. The plunger housing 98 is securely held within this support structure 96 by means of a set screw 97, so that its flange portion 98b lies securely against shoulder 96a thereof, as shown in FIG. 6.

The clamp block normally accomodating the "Y"-shaped pinch member 56 representing the outlet means is somewhat modified here by being provided with an integral extension as shown at 64a. This extension 64a is provided with a bore 94 internally threaded at the lower end but smooth at its upper portion, with lower end accommodating an externally threaded plug 94a to serve as support and adjustment for a further compression spring 93 bearing against the underside of the actuator member 92 accommodated within the smooth portion, as may be clearly observed in FIG. 6. Extension 64a is also provided with a transverse hole 63a to accommodate pin 73 and with a slot 77 to accommodate pin 71 therethrough, as may be best observed with reference to FIG. 7. Furthermore, actuator member 92 is also provided with a slot 95 so as to allow member 92 being displaced with reference to pin 73 whose position is fixed within transverse hole 63a of extension 64a. Pins 71 and 83 protrude through the respective holes 61 and 63 of the side flaps 58 of the "Y"-shaped member 56.

Figure 12:
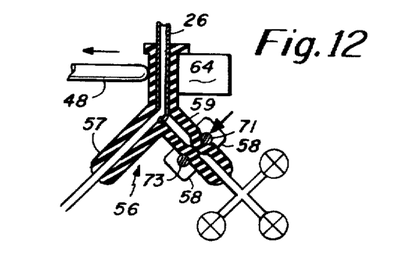

When the rotating arm 24 reaches in its downward travel such that plunger 90 bears against member 92, note FIG. 6, further downward motion by rotating arm 24 will cause the beveled portion 90a to exert a pressure and thereby effect motion of the actuator member 92 within the bore 94 and against compression spring 93, thereby to move also pin 71 within the slot 77 against the respective one leg portion 59 so as to compress the same and the internal channel 53 at that point, substantially as shown in FIG. 12. Fluid then may be introduced through the single inlet means 26 into the leg portion 57 while, at the same time, it is fully assured that nothing passes through the internal channel 53 located in the other leg portion 59. Upon withdrawal of the inlet means 26 from within the entrance portion 54 of the "Y"-shaped member 56, pin 71 also serves to open once again the internal channel 53 by moving the side flap 58 upward due to the action of spring 93. It is only in certain specific instances where this auxiliary closing-off may be required, such as in the use of specific subsystems, e.g., blood gas, co-oximeter of any situation where the presence of even a few bubbles in the sample could cause a problem.

In operation, the multi-position fluid valve of the invention is designed to work as follows.

The single inlet means 26 is in fluid communication by means of a suitable flexible inlet tube 60 with a probe (not shown) designed to be introduced into a suitable receptacle or container having therein a patient's fluid sample which may be blood, serum, plasma, spinal fluid or the like, and is designed as already well known to aspirate a measured amount of such fluid sample by means of a vacuum and transmit the same to the single inlet means 26 of the present invention so as to fill the same. Thereupon, by the use of well-known automatic means such as a microprocessor or mini-computer forming part of the overall analysis apparatus of which the fluid valve is but a part, the single inlet means 26 will be rotated in its oscillatory ambit by means of electric motor 80 and transmitted thereto through shaft 81 turning the "L"-shaped arm 78 and thereby the nonmagnetic post 74 secured to the rotating arm 24 which carries the single inlet means 26, all as previously described. By actuating a specific one of the "Hall"-effect switches 86. the rotational motion imparted to the single inlet means 26 is arrested at the position of the selected outlet means 56 by switch 86 cooperating with the magnet 76, all as well understood in the art. This grossly lines up the blunt needle 26 representing the single inlet means with one of the small holes 52 in the plate 50. At this point, the blunt needle 26 and the pneumatic cylinder 30 together with its surrounding cylindrical cam 44 are in their uppermost extended position as shown in FIG. 1, so that there is sufficient clearance above plate 50, not only for the blunt needle 26, but also for the guide member 28 and plunger 90.

After such gross alignment between a selected one of the outlet means 56 and the blunt needle 26 is effected by the indexing action of the respective "Hall"-effect switch 86 cooperating with the magnet 76, the pneumatic cylinder 30 is actuated to move downward by admitting fluid under pressure, such as air, through air connector 33, all as is well known in the art. Once such relative motion between blunt needle 26 and the inverted "Y"-shaped member 56 is effected, the guide member 28 with its rounded end is the first to enter through the "U"-shaped opening 50a into its respective guide slot 68 formed in the respective clamp block 64, as previously mentioned. The cooperation between guide member 28 and guide slot 68 assures a precise alignment of the blunt needle with the center of the entrance portion 54, so that it can easily and effectively enter the same, and by aligning its side exit port 27 with the internal channel 53 in one of the pair of leg portions, it effectively establishes fluid-tight communication therewith.

Slightly preceding the entrance of the blunt needle 26 into the entrance portion 54 of the respective outlet means 56, the inner end 48c of the respective pinch rod 48 lying adjacent the particular "Y"-shaped member 56 is first permitted to enter into the channel 46 of the cylindrical cam 44, as may be best visualized from FIGS. 1 and 4. By so doing, the other end of pinch rod 48 is gradually moved from its normally closed off position 48a shown in broken lines in FIG. 4, to the fully opened position 48b, at which point end 48c rests at the deepest penetration within channel 46 as shown in FIG. 4.

Once such fluid-tight communication is obtained between blunt neelde 26 and the inverted "Y"-shaped member 56, a discrete amount of the fluid sample contained in needle 26 and flexible tube 60 is removed therefrom by suction being applied through tubing 62, all as well known in the art. When the required precise amount of fluid sample has been transferred from the blunt needle 26 to the respective outlet means 56 which, as already mentioned, also forms a part of and is in communication with a separate and independent fluid subsystem designed to measure for one specific constituent of the fluid sample, the suction force is terminated and blunt needle 26 is caused to be withdrawn from the entrance portion 54, while the same entrance portion 54 is once again closed off by its respective pinch rod 48. The above is accomplished by admitting a source of fluid under pressure, such as air, through air connector 31 into the double acting pneumatic cylinder 30 and cause the same to be once again moved upward from the position shown in FIG. 4 to the position shown in FIG. 1. During this upward travel of cylinder 30 and cam 44, the end 48c of pinch rod 48 is caused gradually to be removed from the channel 46 and be in contact again with the peripheral surface of the cam 44.

At this point, the fluid valve of the invention is ready to dispense a further measure of fluid sample into another one of the outlet means 56. Hence, the indexing means is again actuated, i.e., the electric motor 80 will again effect rotation, either left or right, to the blunt needle 26 transmitted thereto by rotating arm 24 and with the combined action of another one of the "Hall"-effect switches 86 and magnet 76, gross alignment of blunt needle 26 with another selected outlet means 56 is once again effected, with subsequent operation of relative motion therebetween to effect fluid-tight communication therebetween. Discrete quantity of fluid sample transfer from blunt needle 26 to "Y"-shaped member 56 again takes place by suction, as already described. These operational steps are further illustrated in FIGS. 8 through 12.

It is to be understood that outlet means 56 and those without side flaps 58 depicted as 56a form a part also of analytical subsystems which operate independently of one another and have each for their function the determination of one specific constituent of the biological fluid under examination. The particular outlet means 56 represented by the inverted "Y"-shaped member as shown in FIG. 12 is provided with side flaps 58 needed in the operation of the system described with particular reference to FIGS. 6 and 7, but are not normally needed in the others. Hence, the flaps 58 may be conveniently omitted, as shown by members 56a in the FIGS. 8 through 11.

In these views, only selective portions of the inlet and outlet means with their associated operative parts are shown as needed to explain the operation of the fluid valve of the invention. As may be noted in FIG. 8, the pinch rod 48 effectively seals off the entrance portion 54a against the clamp block 64 with the blunt needle 26 representative of the single inlet means being positioned just above the entrance portion 54a. Leg portion 57a may be connected by suitable valve, not shown, to at least three sources under pressure, namely to a flush solution, a calibrating gas medium and a calibrating standard medium, or if desired, singly air under pressure.

Figure 8:
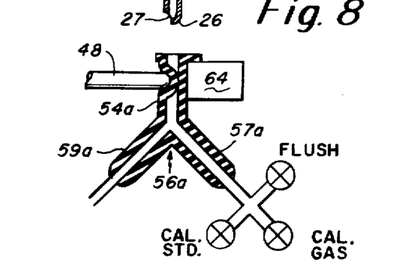
FIGS. 8-12 are representative views of selective portions of the inlet means and one of the outlet means, considered helpful in explaining the operation of the fluid valve of the invention.

Depending upon the operation of the particular analytical subsystem of which this particular outlet means 56a may form a part in the position shown in FIG. 8, either flush solution or calibrating gas medium or calibrating standard medium or air or some combination thereof may be admitted into leg portion 57a and freely transmitted into the other leg portion 59a and by a suitable tubing to the operative portions of the particular analytical subsystem, all as well understood in the art. Since these solutions or mediums are admitted under pressure, no suction need now be applied to the tubing connected to the leg portion 59a.

Figure 9:
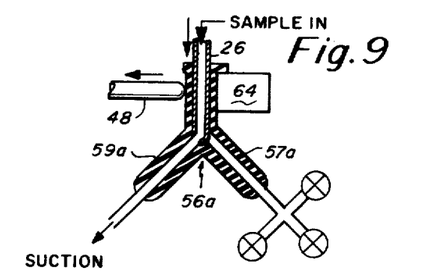

In the position of the operative parts shown in FIG. 9 with the blunt needle 26 fully inserted within the entrance portion 54a so that its side exit port 27 is in communication with the internal channel of the side leg portion 59a, a discrete amount of sample contained in the blunt needle 26 and to the therein connected flexible tube, not shown, is removed therefrom by suction applied through the tubing connected to the side leg portion 59a. The required suction can conveniently be produced by a vacuum system, not shown. At this time, it should be noted that the respective valves connecting the flush solution, calibrating gas medium, calibrating standard medium and air under pressure to the other leg portion 57l are all securely closed off, insuring thereby that only the sample is admitted into the leg portion 59a.

Figure 10:
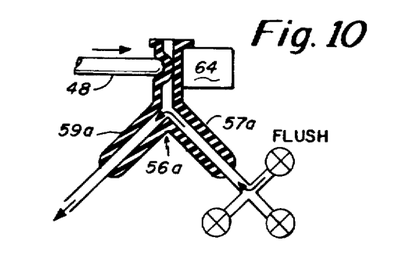

In the position shown in FIG. 10, the pinch rod 48 once again effectively seals off the entrance portion 54a of the outlet means 56a and at the same time, the valve (not shown) operatively connecting the flush solution to the leg portion 57a has been opened so as to admit this flush solution under pressure into the leg portion 57a, and therethrough into the other leg portion 59a. Thereby, the particular analytical subsystem is easily and effectively flushed clean prior to and in preparation for another analysis, all as well known in apparatus of this kind.

Figure 11:
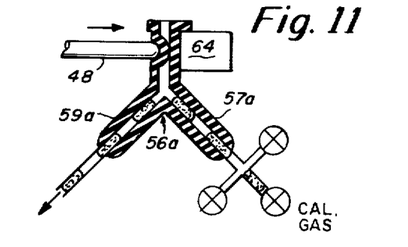

In FIG. 11 there is shown the admission of pulsed calibrating gas through the operation of a different valve (not shown) into the leg portion 57a and therethrough to the other leg portion 59a, with the entrance portion 54a still being securely closed off by the pinch rod 48.

FIG. 12, of course, shows the operation of the modified means shown and described with reference to FIGS. 6 and 7, in that the outlet means 56 here is provided with the pair of side flaps 58 so as to be able to effect closing off by means of the pins 71 and 73, the side leg portion 59 while the blunt needle 26 is in its downward position. Sample fluid is then effectively introduced through suction into the other leg portion 57. By effectively closing off the leg portion 59, a further safety factor is provided in addition to the valved connections (not shown) to the respective flush solution, calibrating gas medium, calibrating standard medium and/or air under pressure, so that none of these can enter the leg portion 59 even if one of the valves were to malfunction.

It will be apparent from the foregoing description that obvious modifications and variations can be made to the multi-position fluid valve of the invention without departing from the spirit and scope of the invention.

Accordingly, the scope of the invention is only to be limited as necessitated by the accompanying claims.

What is claimed is:

1. Fluid valve comprising
   a support structure rotatably supporting a single inlet means comprising a hollow blunt needle having a rounded closed end and being provided with an exit port formed substantially normal to the axis of said needle, and stationarily supporting a plurality of outlets,
   means for effecting communication between said single inlet means and one of said outlets, in which each of said plurality of outlets comprises an entrance portion and a pair of leg portions and in which said communication is effected by said exit port and only one of said pair of leg portions.

2. The fluid valve of claim 1 in which each of said plurality of outlets comprises an inverted "Y"-shaped member formed of an entrance portion and a pair of leg portions.

3. The fluid valve of claim 2 further characterized in that said single inlet means (comprises a blunt needle having a side port and) is designed to be introduced into said entrance portion of said "Y"-shaped member so that its said (side) exit port is in communication with one of said pair of leg portions.

4. The fluid valve of claim 3 further characterized in that said means for effecting communication between said inlet and one of said outlets is a double-acting pneumatic cylinder operative sequentially to thrust said blunt needle into said entrance portion of said "Y"-shaped member so as to effect communications therebetween.

5. The fluid valve of claim 4 being further characterized in being provided also with a means for normally closing off each said entrance portion of each said "Y"-shaped members.

6. The fluid valve of claim 5 in which said means for normally closing off each said entrance portion comprises a cylindrical cam mounted concentrically about said pneumatic cylinder and a plurality of pinch rods operatively mounted adjacent each said entrance portion of each said "Y"-shaped members and cooperating with said cam.

7. The fluid valve of claim 6 being further characterized in that said cam is provided with a channel designed to accommodate therein one end of one of said plurality of pinch rods so as to open thereby said entrance portion of said "Y"-shaped member when said blunt needle is thrust therein.

8. The fluid valve of claim 7 being further characterized in being also provided with indexing means designed selectively to align said blunt needle with one of said entrance portions of said "Y"-shaped members.

9. The fluid valve of claim 8 in which said means for selectively indexing said blunt needle into alignment with one of said entrance portions of said "Y"-shaped members comprises
   a means for rotating said blunt needle in an arc about said pneumatic cylinder,
   electronic means cooperating with a magnet to arrest the rotation of said blunt needle at a selected one of said plurality of outlets,
   a guide pin mounted adjacent said blunt needle, and
   a plurality of guide slots mounted adjacent each of said plurality of outlets,
   whereby said blunt needle is precisely aligned with each said selected entrance portion of said "Y"-shaped member prior to its being thrust therein.

10. The fluid valve of claim 5 being also provided with a means for closing off one of said pair of leg portions of some of said "Y"-shaped members.

11. A fluid valve for channeling small amounts of fluid samples from a single source to one or more or all of a plurality of outlets, with each of said outlets communicating with a separate fluid system comprising
    a support structure designed revolvingly to support a single inlet means comprising a hollow blunt needle having a rounded closed end and being provided with an exit port formed substantially normal to the axis of said needle connected to said single fluid system and stationarily to support a plurality of outlets, in which each of said outlets comprises an inverted "Y"-shaped member formed of an entrance portion and a pair of leg portions, and
    means sequentially effecting communication between said inlet means and one or more or all of said plurality of outlets.

12. The fluid valve of claim 11 being further characterized in that said blunt needle is designed to be introduced into said entrance portion of said "Y"-shaped member so that its said side port is in communication with one of said pair of leg portions.

13. The fluid valve of claim 11 being also provided with a means for normally closing off each of said plurality of outlets comprising
    a cylindrical cam concentrically mounted about said pneumatic cylinder,
    a channel provided in the outer surface of said cylindrical cam and
    a plurality of pinch rods operatively mounted adjacent each said plurality of outlets with one end of said pinch rods designed to be accommodated within said channel,
    whereby when said inlet is in communication with one of said outlets, its associated one pinch rod is accommodated within said channel so as to open thereby said one of said outlets.

14. The fluid valve of claim 11 being further provided with an indexing means designed selectively to align said inlet with one of said pluarality of outlets comprising
    a motor for rotating said inlet in an arc about said cam,
    means for arresting the rotation of said inlet at a selected one of said plurality of outlets,
    a guide member mounted adjacent said inlet, and
    a plurality of guide slots designed selectively to accommodate therein said guide member and mounted adjacent each of said plurality of outlets,
    whereby said inlet is precisely aligned with each said selected one of said outlets when said inlet is being thrust therein.

15. The fluid valve of claim 11 being also provided with a means for closing off one of said pair of leg portions of some of said "Y"-shaped members.

16. A fluid valve for switching fluid samples emanating from a single source to one or more or all of a plurality of outlets in which each of said outlets communicates with a separate and independent fluid system comprising
    a support structure oscillatingly supporting a single inlet means connected to said single source and comprising a hollow blunt needle having a rounded closed end and being provided with an exit port formed substantially normal to the axis of said needle, and fixedly supporting a plurality of outlets in which each of said plurality of outlets comprises an inverted "Y"-shaped member formed of an entrance portion and a pair of leg portions, means for sequentially aligning said inlet means with one or more or all of said plurality of outlets, and means for effecting communication seriatim between said inlet means and said plurality of outlets.

17. The fluid valve of claim 16 which said oscillating support for said inlet means includes a motor having a shaft, means operatively connecting said shaft with said inlet means so as to transmit an oscillatory motion thereto.

18. The fluid valve of claim 16 being further provided with a means for arresting said oscillatory motion transmitted to said inlet means at a selected one of said plurality of outlets.

19. The fluid valve of claim 16 wherein said means for sequentially aligning said inlet means with one or more or all of said plurality of outlets comprises a guide member mounted adjacent said inlet means and a plurality of guide slots each designed to accommodate therein said guide member and mounted adjacent each said plurality of outlets, whereby said inlet means is sequentially aligned with each said selected one of said outlets when said inlet means is introduced into said selected one of said outlets.

20. A fluid valve for switching fluid samples emanating from a single source to one or more or all of a plurality of outlet means in which each of said outlet means communicates with and also forms a part of a separate and independent fluid system, comprising a support structure, a single inlet means mounted for oscillation within a set ambit on said support structure and connected to said single source, said means comprising a hollow blunt needle having a rounded closed end and being provided with an exit port formed substantially normal to the axis of said needle, a plurality of outlet means stationarily supported within said ambit on said support structure, each of said outlet means comprising an entrance portion and a pair of leg portions, means for selectively indexing within said ambit said inlet means so as to be aligned with one of said outlet means, and means for effecting communication between said inlet means and said aligned outlet means.

21. The fluid valve of claim 20 in which said blunt needle is designed to be introduced into said entrance portion of said outlet means so that said side port establishes communication with one of said pair of leg portions.

22. The fluid valve of claim 20 in which said indexing means comprises a motor for imparting an oscillatory motion within said ambit to said inlet means, means for arresting the oscillation of said inlet means, a guide member mounted adjacent said inlet means and being oscillatory therewith, a plurality of guide slots designed selectively to accommodate therein said guide member, with one of said slots mounted adjacent each of said plurality of outlet means, whereby said inlet means is precisely aligned with each said selected one of said outlet means.

23. The fluid valve of claim 20 in which said means for effecting communication includes a pneumatic cylinder operative to introduce said inlet means into a selected one of said plurality of outlet means.

24. The fluid valve of claim 20 being also provided with a means for normally closing off each of said plurality of outlet means comprising a cylindrical cam concentrically mounted about said pneumatic cylinder, a channel provided in the outer surface of said cylindrical cam and in parallel with its longitudinal axis, and a plurality of pinch rods operatively mounted adjacent each said plurality of outlet means in a plane normal to said longitudinal axis and radially projecting therefrom, with one end of said pinch rods designed to be accommodated within said channel, whereby when said inlet means is in communication with one of said outlet means, its said associated one pinch rod is accommodated within said channel so as to open thereby said one of said outlet means.

25. The fluid valve of claim 20 being also provided with a means for closing off one of said pair of leg portions of some of said plurality of outlet means.

26. A fluid valve for switching discrete amounts of a fluid sample introduced through a single source to one or more or all of a plurality of outlets in which each of said outlets is provided with communication to a separate and independent fluid system, comprising a support structure, a single inlet means mounted for oscillatory motion of said support structure and having communication with said source, a plurality of outlet means fixedly mounted on said support structure within the ambit of said inlet means, means for normally closing off each of said outlet means, means for selectively indexing within an ambit so as to line up with one of said outlet means, means for effecting relative motion between said inlet means and said aligned outlet means, means for opening said one aligned outlet means upon effecting said relative motion therebetween and said inlet means, whereby said relative motion also effects communication with said aligned outlet means.

27. The fluid valve of claim 26 in which said single inlet means comprises a blunt needle provided with a side port and each of said plurality of outlet means comprises an inverted "Y"-shaped member formed of an entrance portion and a pair of integral leg portions.

28. The fluid valve of claim 26 being further characterized in that said blunt needle is designed to be thrust into said entrance portion whereupon its said side port is in communication with one of said pair of leg portions.

29. The fluid valve of claim 26 in which said oscillatory motion to said inlet means is imparted thereto by a motor having a shaft, and a means operatively connecting said shaft to said inlet means.

30. The fluid valve of claim 26 in which said means for effecting relative motion between said inlet means and said aligned outlet means inlcudes a pneumatic cylinder whose axis also defines the axis of said oscillatory motion of said inlet means.

31. The fluid valve of claim 26 in which said means for normally closing off each of said outlet means comprises
- a cylindrical cam concentrically mounted about said pneumatic cylinder,
- a channel provided in the outer surface of said cylindrical cam and in parallel with its longitudinal axis, and
- a plurality of pinch rods operatively mounted adjacent each said plurality of outlet means in a plane normal to said longitudinal axis and radially projecting therefrom, with one end of said pinch rods designed to be accommodated within said channel,
- whereby when said inlet means is in communication with one of said outlet means, its said associated one pinch rod is accommodated within said channel so as to open thereby said one of said outlet means.

32. The fluid valve of claim 26 in which said indexing means for said inlet means comprises
- a motor for imparting said oscillatory motion within said oscillatory ambit to said inlet means,
- means for arresting the oscillation of said inlet means,
- a guide member mounted adjacent said inlet means and being oscillatory therewith,
- a plurality of guide slots designed selectively to accommodate therein said guide member, with one of said slots mounted adjacent each of said plurality of outlet means,
- whereby said inlet means is precisely aligned with each said selected one of said outlet means.

33. The fluid valve of claim 27 being also provided with a means for closing off one of said pair of leg portions of some of said "Y"-shaped members.

* * * * *